United States Patent [19]

Shigeyasu et al.

[11] 4,189,603

[45] Feb. 19, 1980

[54] PROCESS FOR PRODUCING HIGH-QUALITY TEREPHTHALIC ACID SUITABLE FOR USE IN DIRECT POLYMERIZATION

[75] Inventors: Motoo Shigeyasu; Hatsutaro Yamazaki; Takehiko Kitamura, all of Matsuyama, Japan

[73] Assignees: Matsuyama Petrochemicals Inc.; Maruzen Oil Co., Ltd., both of Osaka, Japan

[21] Appl. No.: 944,216

[22] Filed: Sep. 20, 1978

[30] Foreign Application Priority Data

Sep. 20, 1977 [JP] Japan ................................. 52-113715

[51] Int. Cl.$^2$ .............................................. C07C 51/42
[52] U.S. Cl. ...................................... 562/417; 562/421
[58] Field of Search ................................ 562/417, 421

[56] References Cited

U.S. PATENT DOCUMENTS 3,284,493  11/1966  Chibnik ................................ 562/417

*Primary Examiner*—Alan Siegel
*Attorney, Agent, or Firm*—Sughrue, Rothwell, Mion, Zinn and Macpeak

[57] ABSTRACT

A process for producing terephthalic acid of high quality suitable for use in direct polymerization comprising oxidizing a para-dialkylbenzene and/or an oxidized intermediate thereof in the liquid phase with molecular oxygen or a molecular oxygen-containing gas in the presence of an oxidation catalyst containing a heavy metal in a lower aliphatic carboxylic acid solvent, the reaction being carried out in the presence of a specified amount of a phenol. Polyesters prepared from the resulting terephthalic acid have good color.

23 Claims, No Drawings

PROCESS FOR PRODUCING HIGH-QUALITY TEREPHTHALIC ACID SUITABLE FOR USE IN DIRECT POLYMERIZATION

BACKGROUND OF THE INVENTION

1. Field of the Invention

This invention relates to a process for producing terephthalic acid. More specifically, it relates to a process for producing terephthalic acid providing terephthalic acid of high quality capable of being used to produce a polymer of good color when used in direct polymerization, and in which loss of the reaction solvent by combustion is reduced.

2. Description of the Prior Art

Various methods have been suggested heretofore for producing terephthalic acid of high quality for use in direct polymerization by simply oxidizing a para-dialkylbenzene and/or an oxidized intermediate thereof with molecular oxygen or a molecular oxygen-containing gas in the liquid phase in the presence of an oxidation catalyst in a lower aliphatic carboxylic acid solvent (e.g., as disclosed in Japanese Patent Publication No. 36732/70, U.S. Pat. No. 3,846,487 and Japanese Patent Application (OPI) Nos. 106833/77, 26240/74, 80531/73 (The term "OPI" as used herein refers to a "published unexamined Japanese patent application"), etc.). These prior methods, however, are not entirely satisfactory for the production of high quality terephthalic acid for direct polymerization. For example, a large loss of the reaction solvent occurs due to combustion. Or when the resulting terephthalic acid is used to produce a polyester by the so-called direct polymerization method which comprises esterifying the terephthalic acid directly with ethylene glycol without proceeding through dimethyl terephthalate, and polycondensing the esterification product, e.g., as disclosed in Japanese Patent Publication No. 19314/75, the resulting polyester does not always have uniform color.

In recent years, the direct polymerization method has become increasingly used for production of polyesters, and the trend is toward the employment of a continuous direct polymerization method which is economically more advantageous than the batchwise method. Under these circumstances, the conditions as to quality required of the starting terephthalic acid are more rigorous, and the quality of the starting terephthalic acid should be so high and uniform that its use in the direct polymerization method provides over long periods of time polyesters having an industrially reproducible uniform quality and good color. However, since the oxidation reaction of a para-dialkylbenzene and/or an oxidized intermediate thereof for the production of terephthalic acid is a radical chain reaction, various impurities may be formed in addition to the reaction intermediates or colored materials and may be included in the final terephthalic acid. Such terephthalic acid when used results in polyesters with poor color when directly polymerized continuously. This inconvenience frequently occurs in the conventional method for producing terephthalic acid for direct polymerization depending upon the reaction conditions and is especially frequent when terephthalic acid is produced continuously over relatively long periods of time.

In order to obtain polyesters with uniform quality and good color by direct polymerization, it is important to control the production of terephthalic acid used as a starting material. Simply checking the 4-carboxybenzaldehyde content of the desired terephthalic acid, and determining the color as a solid or a solution are insufficient as is the case using conventional techniques. Terephthalic acid having a low 4-carboxybenzaldehyde content and good color as a solid or solution sometimes results in a polyester having poor color when such is produced by the direct polymerization method.

SUMMARY OF THE INVENTION

An object of this invention is to provide a process for producing high-quality terephthalic acid.

Another object of this invention is to provide a process for continuously producing over a long period of time terephthalic acid which always has a uniform high-quality.

A further object of this invention is to provide a process for producing economically high-quality terephthalic acid by reducing combustion loss of the reaction solvent.

Still a further object of this invention is to provide a process for producing high-quality terephthalic acid which is suitable for producing a polyester having uniform quality and good color using the direct polymerization method.

It has been found that the above objects are achieved by producing terephthalic acid in the presence of $3 \times 10^{-5}$ to $700 \times 10^{-5}$ mole/liter, based on the volume of the reaction solvent, of a phenol.

Accordingly, this invention provides a process for producing terephthalic acid of high-quality suitable for use in direct polymerization, which comprises oxidizing a paradialkylbenzene and/or an oxidized intermediate thereof in the liquid phase with molecular oxygen or a molecular oxygen-containing gas in the presence of an oxidation catalyst containing a heavy metal in a lower aliphatic carboxylic acid solvent, wherein the reaction is carried out in the presence of $3 \times 10^{-5}$ to $700 \times 10^{-5}$ mole/liter, based on the volume of the solvent, of a phenol.

DETAILED DESCRIPTION OF THE INVENTION

Generally, phenols are known to inhibit oxidation reactions. It has now been found that the presence of an appropriate amount of a phenol in the liquid-phase oxidation of a para-dialkylbenzene and/or an oxidized intermediate thereof does not greatly adversely affect the desired oxidation reaction, but rather inhibits side-reactions and facilitates uniform maintenance of the quality of terephthalic acid over a long period of time and a reduction in loss of the reaction solvent by combustion.

The amount of the phenol present in the reaction system is $3 \times 10^{-5}$ to $700 \times 10^{-5}$ mole/liter, preferably $5 \times 10^{-5}$ to $500 \times 10^{-5}$ mole/liter, more preferably $10 \times 10^{-5}$ to $360 \times 10^{-5}$ mole/liter, based on the reaction solvent. When the amount of the phenol is less than $3 \times 10^{-5}$ mole/liter, the amount of impurities in the terephthalic acid produced is generally small, and a polyester obtained from the resulting terephthalic acid by the direct polymerization method has good color. However, the terephthalic acid is affected by even a slight fluctuation in the oxidation reaction conditions, and it is not easy to maintain uniformly the quality of terephthalic acid over a long period of time. Furthermore, the process is not economical because loss of the reaction solvent by combustion increases. On the other hand, when the amount of the phenol is larger than $700 \times 10^{-5}$ mole/liter, loss of the reaction solvent by combustion is decreased, and the process becomes economical. However, the resulting terephthalic acid contains a large amount of impurities, and polyesters prepared from the terephthalic acid by the direct polymerization method have poor color.

Examples of phenols which can be employed in the reaction system are phenols and hydroquinones, etc., each of which can be either unsubstituted or substituted with one or more alkyl groups containing 1 to 3 carbon atoms, e.g., straight chain or branched chain alkyl groups, such as methyl, ethyl, n-propyl and isopropyl, etc., groups. More specifically, examples of phenols which can be employed in the reaction system are monohydric phenols, either unsubstituted or substituted with one or more alkyl groups containing 1 to 3 carbon atoms, such as phenol, cresol, dimethylphenol, trimethylphenol, ethylphenol, isopropylphenol and n-propylphenol and polyhydric phenols, either unsubstituted or substituted with one or more alkyl groups containing 1 to 3 carbon atoms, such as hydroquinone, resorcinol, catechol, pyrogallol, methylhydroquinone, ethylhydroquinone, isopropylhydroquinone and n-propylhydroquinone. Mixtures of these compounds can also be used. The term "phenol" will be used herein to collectively describe both monohydric phenols and polyhydric phenols.

In the performance of the process of this invention, the starting para-dialkylbenzene and/or an oxidized intermediate thereof, the lower aliphatic carboxylic acid solvent and the oxidation catalyst may be those materials generally used in the production of terephthalic acid for direct polymerization, e.g., as disclosed in Japanese Patent Publication No. 36732/70, Japanese Patent Application (OPI) Nos. 26240/74, 80531/73, and 106833/77, and U.S. Pat. No. 3,846,487. Specifically, p-dialkylbenzenes having 1 to 4 carbon atoms in each alkyl group can be used. Suitable examples of such alkyl groups include straight chain and branched chain alkyl groups, such as methyl, ethyl, n-propyl, isopropyl, n-butyl and isobutyl groups. For example, p-xylene and p-diisopropylbenzene can be used as the p-dialkylbenzene. Of these, p-xylene is most preferred. The term "oxidized intermediate thereof" is used herein to describe intermediates produced by oxidation of p-dialkylbenzenes and derivatives of p-alkylbenzenes containing oxygen. p-Toluic acid and p-toluic aldehyde is an example of a suitable oxidized intermediate of a p-dialkylbenzene which can be used. Suitable lower aliphatic carboxylic acid solvents which can be used include those having 1 to 8, preferably 2 to 4, carbon atoms, for example, acetic acid, propionic acid, and butyric acid. Monocarboxylic acids are preferred and acetic acid is especially preferred. A suitable amount of the lower aliphatic carboxylic acid is more than 2 times, preferably 3 to 6 times, the weight of the p-dialkylbenzene and/or the weight of the oxidized intermediate thereof, calculated as the weight of the p-dialkylbenzene from which it is derived. The lower aliphatic carboxylic acid solvent may contain less than about 20% by weight of water.

The oxidation catalyst is preferably a catalyst containing bromine and at least one heavy metal, such as cobalt, manganese, copper, nickel, chromium, iron, zinc, cadmium, cerium, lead, etc., preferably cobalt and/or manganese, more preferably a combination of cobalt and manganese. Compounds of heavy metals which can be used as oxidation catalysts in the oxidation reaction include inorganic salts, such as halides (e.g., bromides or chlorides such as cobalt bromide, manganese bromide, cobalt chloride, manganese chloride, etc.) and carbonates (e.g., cobalt carbonate or manganese carbonate, etc.), naphthenic acid salts (e.g., cobalt naphthenate, manganese naphthenate, etc.), phthalic acid salts (e.g., cobalt phthalate, manganese phthalate, etc.), and lower aliphatic carboxylic acid salts (e.g., manganese acetate, cobalt acetate, etc.), which are soluble in the lower aliphatic carboxylic acid used as a solvent. Suitable bromine compounds which can be used include ammonium salts, inorganic salts, such as sodium or potassium salts, organic bromides, such as tetrabromoethane, bromoform, dibromoacetic acid, bromo-p-xylene, etc., and hydrogen bromide which are soluble in the lower aliphatic carboxylic acid solvent. Bromine can also be used as a bromine source. Compounds providing a source of bromine as well as providing a source of cobalt or manganese, such as cobalt bromide or manganese bromide, are preferred.

A suitable amount of the oxidation catalyst is such that the amount of the catalytic heavy metal, such as cobalt or manganese, is about 0.01 to about 3.0% by weight, calculated as metal, based on the weight of the lower aliphatic carboxylic acid solvent, and a suitable amount of bromine, calculated as atomic bromine, is about 1 to about 8 times the weight of the catalytic heavy metal. Where the oxidation catalyst contains cobalt and manganese, the cobalt is used preferably in an amount of 0.01 to 0.5% by weight, calculated as the metal, based on the weight of the lower aliphatic carboxylic acid solvent, and the manganese is used preferably in an amount of 1 to 500% by weight, calculated as the metal, based on the cobalt. An organic promotor, such as an aldehyde (e.g., p-aldehyde, acetaldehyde, propyl aldehyde and the like) or a ketone (e.g., methyl ethyl ketone and the like) may be used in combination with the oxidation catalyst, if desired. A suitable amount of the organic promotor which can be used is about 1 to 30% by weight, preferably 2 to 20% by weight, based on the weight of the solvent.

A suitable reaction temperature is about 80° to about 230° C., preferably 150° to 220° C., more preferably 180° to 210° C.

A suitable reaction pressure is a reaction pressure at which the reaction can be performed in the liquid phase, i.e., a pressure at which the p-dialkylbenzene and/or an oxidized intermediate thereof and the lower aliphatic carboxylic acid solvent are in the liquid phase.

A gas containing about 5 to about 100 volume%, preferably 10 to 40 volume%, of molecular oxygen can be used as the molecular oxygen or molecular oxygen-containing gas. A suitable molecular oxygen or molecular oxygen-containing gas feed rate is such that the molecular oxygen is fed at a rate of about 0.75 to about 1.3 $Nm^3$ per kg of the p-dialkylbenzene. Suitable gases other than molecular oxygen which can be present in the molecular oxygen-containing gas include nitrogen gas, carbon dioxide, rare gases, such as neon and helium etc., combustion gas of hydrocarbon containing carbon dioxide and carbon monoxide, etc., and exhaust gas from the reactor. For commercial operations, air is preferably used as the molecular oxygen or molecular oxygen-containing gas. Preferably, the air is fed into the reaction system at a feed rate of 3.8 to 6.0 $Nm^3$ per kg of the p-dialkylbenzene. A suitable residence time of the starting p-dialkylbenzene and/or an oxdized intermediate thereof is about 0.5 to about 5 hours.

The phenol can be added to the reaction system and the amount of the phenol can be adjusted to achieve an amount of $3 \times 10^{-5}$ to $700 \times 10^{-5}$ mole/liter based on the reaction solvent. Alternatively, specified amount of the phenol may be formed in the oxidation reaction system by adjusting the oxidation reaction conditions. Alternatively, both of these methods may be used together to achieve the specified amount of the phenol in the reaction system. However, the phenol is preferably fed into the reaction system. The phenol can be fed into the reaction system for a short period only at the beginning of the reaction or can be fed into the reaction system throughout the reaction. Continuously feeding the phenol throughout the reaction is preferred to reduce loss of the reaction solvent by combustion. The above specified amount of the phenol achieved in the reaction system by adjusting the oxidation reaction conditions can be accomplished by appropriately adjusting one or more of the oxidation reaction conditions, such as the reaction temperature, the concentration of the catalyst, the feed rate of molecular oxygen or molecular oxygen-containing gas, for example, the air, the residence time of the starting material in the reaction system, the water content of the reaction solvent, and the degree of dispersion of materials to be oxidized (e.g., the starting material) and the molecular oxygen or the molecular oxygen-containing gas. The amount of the phenol to be formed in the reaction system, which is related to the various reaction conditions described above, generally increases with increasing reaction temperatures, and decreases with increasing concentration of the catalyst. Furthermore, when the feed rate of the molecular oxygen or molecular oxygen-containing gas is increased, the amount of the phenol formed decreases (the feed rate should be limited to a value such that the concentration of excess oxygen in the exhaust gas is not more than about 8% by volume and does not exceed the explosive limit). The amount of the phenol formed also decreases as the residence time of the starting material in the reaction system increases and as the water content of the reaction solvent decreases. The reaction temperature, the concentration of the catalyst, the feed rate of the molecular oxygen or molecular oxygen-containing gas, for example, the air, the residence time of the starting material in the reaction system, and the water content of the reaction solvent should be selected from the ranges set forth hereinabove. The amount of the phenol formed tends to decrease when the degree of dispersion of the materials to be oxidized (e.g., the starting material) and the degree of dispersion of the molecular oxygen or molecular oxygen-containing gas increases.

According to this invention, highly pure terephthalic acid always having a uniform quality can be continuously produced in a stable manner. The terephthalic acid obtained by the present invention can be used to produce polyesters always having a uniform quality and good color employing the direct polymerization method. Furthermore, the loss of the reaction solvent due to combustion can be reduced, and terephthalic acid can be prepared more economically than in conventional methods.

The amount of the phenol present in the reaction system as set forth in the present invention is measured by the Koppeschaar method known as a method for determining phenols and described, for example, in Seiji Takagi, "Yoryo Bunseki no Jikken to Kaiseki" ("Experiments and Calculations in Volumetric Analyses") Yoryo Bunseki (Volumetric Analyses), Vol. 2, p. 299 (1962). The sample used is a sample of the liquid portion of the reaction mixture which is obtained by withdrawing a sample of the reaction mixture from the reaction system, and subjecting the sample to solid-liquid separation. The measurement temperature is 0° C., and it is assumed in the calculation that 1 mole of the phenol corresponds to 4 equivalents of Br.

Heretofore, determining the quality of terephthalic acid using only the 4-carboxybenzaldehyde content in the terephthalic acid and the color of the terephthalic acid as a solid or a solution has been insufficient. Thus, in this invention, the color of the polyester obtained from the terephthalic acid is also used to check the quality of the terephthalic acid.

The terephthalic acid produced in the present invention is reacted with ethylene glycol to form an ester, and subsequently the ester is polycondensed to produce a polyester. The direct polymerization of terephthalic acid in this manner is disclosed, for example, in Japanese Patent Application (OPI) No. 128397/76, Japanese Patent Publication Nos. 6496/75, 19314/75 and 32274/75.

The following Examples and Comparative Examples are given to illustrate the present invention in greater detail. In these examples, all parts, percents, ratios and the like are by weight unless otherwise indicated.

EXAMPLE 1

An oxidation reactor equipped with a reflux condenser, a stirrer, a heating device, a starting material feed inlet, a gas inlet, an inlet for a solvent containing a catalyst, and an outlet for withdrawing the reaction product was continuously charged with 1 part of p-xylene, 3 parts of acetic acid, and a catalyst comprising 0.025 part of cobalt bromide hexahydrate ($CoBr_2 \cdot 6H_2O$), 0.00054 part of manganese acetate tetrahydrate ($Mn(CH_3COO)_2 \cdot 4H_2O$) and 0.0039 part of a 47% by weight aqueous solution of hydrogen bromide, in an amount of 0.0045 part of cobalt (as the metal), 0.00012 part of manganese (as the metal), and 0.014 part of bromine (as atomic bromine), and an oxidation reaction was performed so that the residence time of the p-xylene starting material in the oxidation reactor became 150 minutes. Air was used as an oxidizing gas and the air was fed into the reaction system in an amount of 4.2 N liters/g of p-xylene. The reaction temperature and the pressure were controlled at about 195° C. and 16 kg/cm² so that the amount of the phenol present in the reaction system was $120 \times 10^{-5}$ mole/liter of acetic acid. After the oxidation reaction has reached a steady state, the reaction mixture was subjected to a solid-liquid separation, and the terephthalic acid separated was washed and dried. The properties of the resulting terephthalic acid and the amount of the phenol present in the reaction mixture are shown in Table 1 below. The loss of acetic acid by combustion in the oxidation reaction in the steady state is also shown in Table 1 below.

The resulting terephthalic acid was directly esterified with 1.15 moles, per mole of the terephthalic acid, of ethylene glycol at 250° C. and 2.5 kg/cm². The esterification product was polycondensed at 280° C. under a high vacuum of less than 1 mm Hg using 0.03 part of antimony trioxide and 0.02 part of cobalt acetate per 100 parts of the esterification product to form a polyester. The color of the polyester was measured, and the results are shown in Table 1 below.

EXAMPLE 2

The procedures of Example 1 were repeated except as specifically indicated below. The oxidation reactor was charged continuously with 1 part of p-xylene, 3 parts of acetic acid, and a catalyst comprising 0.0063 part of cobalt acetate tetrahydrate ($Co(CH_3COO)_2 \cdot 4H_2O$), 0.0067 part of manganese acetate tetrahydrate ($Mn(CH_3COO)_2 \cdot 4H_2O$), and 0.0108 part of tetrabromoethane ($Br_2CHCHBr_2$), in an amount of 0.0015 part of cobalt (as the metal), 0.0015 part of manganese (as the metal) and 0.01 part of bromine (as atomic bromine). The reaction temperature was about 210° C. and the reaction pressure was about 23 kg/cm². The amount of the phenol in the reaction system was set at $300 \times 10^{-5}$ mole/liter of the acetic acid solvent.

The properties of the resulting terephthalic acid, the amount of the phenol present in the reaction mixture, the loss of acetic acid due to combustion, and the color of the polyester prepared from the resulting terephthalic acid by the direct polymerization method are shown in Table 1 below.

It can be easily seen from the experimental results obtained in Examples 1 and 2 that good results can be achieved when the amount of the phenol is maintained within the range set forth in the present invention.

Comparative Example 1

The procedures described in Example 1 were repeated except that 0.0021 part of cresol was added to the reaction system, and the desired amount of the phenols present in the reaction system was set at $750 \times 10^{-5}$ mole/liter of the solvent. The results obtained are shown in Table 1 below.

It can be easily seen from the results obtained in this comparative example that when the amount of the phenol in the reaction system is above the upper limit set forth in the present invention, the desired effect is not obtained.

EXAMPLE 3

The procedures of Example 1 were repeated except that 0.0006 part of a 1:1 (molar) mixture of phenol and cresol was added to the reaction system, and the desired amount of the phenols present in the reaction system was set at $300 \times 10^{-5}$ mole/liter of the acetic acid solvent. The results obtained are shown in Table 1 below.

In Example 3, the phenols were added to the reaction system and the amount of the phenols in the reaction system was larger than that in Example 1 but was within the range set forth in this invention. A polyester prepared from the resulting terephthalic acid using the direct polymerization method had good color, the same as that in Example 1, and the loss of the acetic acid solvent due to combustion was less than that in Example 1. It can be easily seen from these results that the addition of phenols is effective in this invention.

Comparative Example 2

The procedures of Example 1 were repeated except that the concentration of the catalyst was 4 times larger as that used in Example 1, the reaction temperature was set at about 190° C., and the amount of the phenol was set at $2 \times 10^{-5}$ mole/liter of the acetic acid solvent. The results obtained are shown in Table 1 below.

The results clearly demonstrate that when the amount of the phenol in the reaction system is less than the lower limit set forth in the present invention, the loss of the reaction solvent due to combustion increases, and a variation occurs in the color of a polyester prepared from the resulting terephthalic acid by the direct polymerization method.

EXAMPLE 4

The procedures described in Example 1 were repeated except the reaction was performed while maintaining the reaction temperature constant at 195° C. There was an indication of an increase in the amount of the phenol present in the reaction system. Accordingly, 170 hours after a steady state had been achieved, the residence time was changed from 150 minutes to 180 minutes, and the amount of the phenol in the reaction system was set at $150 \times 10^{-5}$ mole/liter of the acetic acid solvent. The other conditions and procedures were as set forth in Example 1. The results obtained are shown in Table 1 below.

It can be readily seen from the results obtained in Example 4 that even when the properties (the 4-carboxybenzaldehyde content and the color difference b value) of the resulting terephthalic acid varied somewhat, the color of a polyester prepared from the terephthalic acid by the direct polymerization can be always maintained good if the amount of the phenol in the reaction system is controlled.

EXAMPLE 5

The procedures described in Example 1 were repeated but the reaction was carried out while maintaining the reaction temperature constant at 195° C. There was an indication of an increase in the amount of the phenol in the reaction system. Accordingly, 150 hours after a steady state had been reached, the amount of air fed was charged from 4.2 N liters/g of p-xylene to 4.5 N liters/g of p-xylene. Otherwise, the conditions and procedures employed in Example 1 were used. The results obtained are shown in Table 1 below.

EXAMPLE 6

The procedures of Example 1 were repeated except that the catalyst was employed at a concentration two times larger than that employed in Example 1, and the amount of the phenol present in the reaction system was set at $10 \times 10^{-5}$ mole/liter of the acetic acid solvent. The results obtained are shown in Table 1 below.

EXAMPLE 7

The procedures described in Example 3 were repeated except that the addition of the mixture of phenol and cresol was continued for 150 hours after a steady state had been reached and thereafter the reaction was carried out without the addition of the mixture of phenol and cresol while the amount of the phenol present in the reaction system was set at $300 \times 10^{-5}$ mole/liter of the acetic acid solvent during oxidation reaction. Otherwise, the conditions and procedures employed in Example 3 were used. The results obtained are shown in Table 1 below.

Table 1

| Example or Comparative Example | Reaction Time after Steady State Reached (hours) | Reaction Temperature (°C.) | Properties of Terephthalic Acid 4-Carboxybenzaldehyde Content (ppm) | Properties of Terephthalic Acid Color Difference (b value) | Amount of Phenol in Reaction System ($\times 10^{-5}$ m/l acetic acid) | Combustion* Loss of Acetic Acid (%/hr) | Color** of Polyester (b value) | Remarks |
|---|---|---|---|---|---|---|---|---|
| Example 1 | | | | | | | | |
| | 0 | 195 | 300 | 2.0 | 100 | 3.33 | 2.5 | |
| | 50 | 195 | 290 | 2.1 | 140 | 3.33 | 2.6 | |
| | 100 | 195 | 300 | 2.1 | 180 | 3.29 | 2.6 | |
| | 150 | 194 | 320 | 2.0 | 120 | 3.33 | 2.6 | |
| | 200 | 192 | 340 | 1.9 | 90 | 3.29 | 2.5 | |
| | 300 | 195 | 290 | 2.0 | 150 | 3.33 | 2.6 | |
| | 400 | 194 | 300 | 2.0 | 120 | 3.29 | 2.6 | |
| | 500 | 194 | 300 | 2.0 | 110 | 3.29 | 2.5 | |
| Example 2 | | | | | | | | |
| | 0 | 210 | 370 | 2.0 | 300 | 3.46 | 2.5 | |
| | 50 | 210 | 380 | 2.1 | 340 | 3.46 | 2.5 | |
| | 100 | 208 | 380 | 1.9 | 320 | 3.42 | 2.6 | |
| | 150 | 206 | 370 | 2.0 | 290 | 3.42 | 2.5 | |
| | 200 | 206 | 380 | 1.9 | 300 | 3.38 | 2.5 | |
| | 300 | 208 | 370 | 2.0 | 300 | 3.42 | 2.6 | |
| | 400 | 207 | 370 | 2.1 | 300 | 3.42 | 2.5 | |
| | 500 | 210 | 360 | 2.0 | 300 | 3.46 | 2.6 | |
| Comparative Example 1 | | | | | | | | |
| | 0 | 195 | 370 | 2.1 | 740 | 2.85 | 3.6 | |
| | 50 | 195 | 340 | 2.0 | 730 | 2.80 | 3.5 | |
| | 100 | 195 | 350 | 2.0 | 780 | 2.85 | 3.6 | |
| | 150 | 195 | 370 | 2.1 | 800 | 2.79 | 3.7 | |
| | 200 | 194 | 370 | 2.0 | 770 | 2.80 | 3.6 | |
| | 300 | 194 | 370 | 2.0 | 750 | 2.85 | 3.6 | |
| | 400 | 195 | 360 | 2.0 | 740 | 2.80 | 3.5 | |
| | 500 | 195 | 350 | 2.1 | 750 | 2.80 | 3.6 | |
| Example 3 | | | | | | | | |
| | 0 | 195 | 310 | 2.1 | 270 | 3.07 | 2.6 | Phenol added |
| | 50 | 195 | 320 | 2.0 | 310 | 3.07 | 2.6 | " |
| | 100 | 195 | 310 | 2.1 | 340 | 3.02 | 2.5 | " |
| | 150 | 193 | 300 | 2.0 | 250 | 2.98 | 2.5 | " |
| | 200 | 193 | 290 | 1.9 | 270 | 2.98 | 2.6 | " |
| | 300 | 194 | 310 | 2.0 | 270 | 3.02 | 2.5 | " |
| | 400 | 194 | 300 | 2.1 | 300 | 3.07 | 2.5 | " |
| | 500 | 194 | 290 | 2.0 | 300 | 3.02 | 2.5 | " |
| Comparative Example 2 | | | | | | | | |
| | 0 | 190 | 290 | 1.9 | 2 | 4.22 | 2.0 | |
| | 50 | 190 | 300 | 1.8 | 1> | 4.36 | 2.4 | |
| | 100 | 190 | 300 | 2.0 | 1> | 4.36 | 1.5 | |
| | 150 | 190 | 290 | 1.9 | 1 | 4.22 | 2.3 | |
| | 200 | 190 | 300 | 1.9 | 2 | 4.22 | 2.7 | |
| | 300 | 189 | 290 | 2.0 | 1> | 4.31 | 1.4 | |
| | 400 | 190 | 300 | 2.0 | 2 | 4.27 | 2.0 | |
| Example 4 | | | | | | | | |
| | 0 | 195 | 300 | 2.0 | 100 | 3.33 | 2.5 | Residence Time: 150 minutes |
| | 50 | 195 | 310 | 1.9 | 150 | 3.29 | 2.6 | Residence Time: 150 minutes |
| | 100 | 195 | 300 | 2.0 | 240 | 3.29 | 2.5 | Residence Time: 150 minutes |
| | 150 | 195 | 310 | 2.0 | 370 | 3.20 | 2.7 | Residence Time: 150 minutes |
| | 200 | 195 | 260 | 2.1 | 220 | 3.29 | 2.6 | Residence Time: 180 minutes |
| | 300 | 195 | 250 | 2.0 | 150 | 3.38 | 2.5 | Residence Time: 180 minutes |
| | 400 | 195 | 250 | 1.9 | 160 | 3.42 | 2.6 | Residence Time: 180 minutes |
| | 500 | 195 | 250 | 2.0 | 150 | 3.42 | 2.5 | Residence Time: 180 minutes |
| Example 5 | | | | | | | | |
| | 0 | 195 | 300 | 1.9 | 100 | 3.29 | 2.5 | |
| | 50 | 195 | 310 | 2.0 | 140 | 3.29 | 2.5 | Amount of air: 4.2 N l/g of p-xylene |
| | 100 | 195 | 300 | 1.9 | 230 | 3.29 | 2.6 | |
| | 150 | 195 | 300 | 2.1 | 400 | 3.20 | 2.7 | |
| | 200 | 195 | 300 | 1.9 | 210 | 3.42 | 2.5 | |
| | 300 | 195 | 310 | 2.0 | 130 | 3.47 | 2.5 | Amount of air: 4.5 N l/g of p-xylene |
| | 400 | 195 | 320 | 2.0 | 120 | 3.47 | 2.6 | |
| | 500 | 195 | 300 | 2.0 | 130 | 3.47 | 2.5 | |
| Example 6 | | | | | | | | |
| | 0 | 195 | 250 | 1.8 | 10 | 3.60 | 2.5 | |
| | 50 | 195 | 240 | 1.9 | 15 | 3.60 | 2.5 | |
| | 100 | 195 | 250 | 2.0 | 21 | 3.56 | 2.4 | |

Table 1-continued

| Example or Comparative Example | Reaction Time after Steady State Reached (hours) | Reaction Temperature (°C.) | Properties of Terephthalic Acid | | Amount of Phenol in Reaction System ($\times 10^{-5}$ m/l acetic acid) | Combustion* Loss of Acetic Acid (%/hr) | Color** of Polyester (b value) | Remarks |
|---|---|---|---|---|---|---|---|---|
| | | | 4-Carboxybenz-aldehyde Content (ppm) | Color Difference (b value) | | | | |
| | 150 | 193 | 260 | 2.0 | 9 | 3.60 | 2.5 | |
| | 200 | 193 | 270 | 2.0 | 8 | 3.60 | 2.6 | |
| | 300 | 194 | 250 | 2.1 | 10 | 3.69 | 2.5 | |
| | 400 | 194 | 250 | 2.0 | 10 | 3.69 | 2.5 | |
| | 500 | 195 | 240 | 1.9 | 9 | 3.73 | 2.5 | |
| Example 7 | | | | | | | | |
| | 0 | 195 | 300 | 2.1 | 290 | 3.05 | 2.6 | Phenol added |
| | 50 | 195 | 310 | 2.0 | 300 | 3.07 | 2.6 | " |
| | 100 | 195 | 320 | 2.1 | 310 | 3.00 | 2.5 | " |
| | 150 | 195 | 310 | 1.9 | 330 | 3.02 | 2.6 | " |
| | 200 | 195 | 300 | 2.0 | 310 | 3.07 | 2.5 | No phenol added |
| | 300 | 195 | 300 | 2.0 | 300 | 3.09 | 2.6 | " |
| | 400 | 195 | 310 | 2.1 | 310 | 3.08 | 2.5 | " |
| | 500 | 195 | 300 | 2.0 | 310 | 3.08 | 2.5 | " |

*The loss of acetic acid due to combustion was calculated from the amounts of CO and $CO_2$ measured in the exhaust gas from the oxidation reactor, and the combustion loss of the acetic acid was determined as a proportion of the amount of acetic acid which was found per hour in the exhaust gas based on the amount of acetic acid which was present in the oxidation reactor.

**The polyester was made into chips, and reflected light from the chips was measured using a color difference meter, (Model CM-20, made by Color Machine Co., Ltd.). The b value shows the degree of yellowness, and the smaller the b value is, the better the color of the polyester is.

While the invention has been described in detail and with reference to specific embodiments thereof, it will be apparent to one skilled in the art that various changes and modifications can be made therein without departing from the spirit and scope thereof.

What is claimed is:

1. A process for producing terephthalic acid of high quality for use in direct polymerization, which comprises oxidizing a para-dialkylbenzene and/or an oxidized intermediate thereof in the liquid phase with molecular oxygen or a molecular oxygen-containing gas in the presence of an oxidation catalyst containing a heavy metal in a lower aliphatic carboxylic acid solvent, wherein the reaction is carried out in the presence of a phenol in an amount of $3 \times 10^{-5}$ to $700 \times 10^{-5}$ mole of phenol per liter of the lower aliphatic carboxylic acid solvent at a reaction temperature of about 80° to about 230° C.

2. The process of claim 1, wherein the phenol is added to the reaction system to adjust the amount of the phenol in the reaction system.

3. The process of claim 1, wherein the amount of the phenol is $5 \times 10^{-5}$ to $500 \times 10^{-5}$ mole of phenol per liter of the lower aliphatic carboxylic acid solvent.

4. The process of claim 1, wherein the phenol is a monohydric phenol or a polyhydric phenol, each of which may be unsubstituted or substituted with one or more of an alkyl group having 1 to 3 carbon atoms.

5. The process of claim 1, wherein the alkyl group of the p-dialkylbenzene has 1 to 4 carbon atoms.

6. The process of claim 1, wherein the oxidized intermediate of the p-dialkylbenzene is selected from the group consisting of p-toluic acid and p-toluic aldehyde.

7. The process of claim 1, wherein the molecular oxygen-containing gas contains about 5 to about 100% by volume of molecular oxygen based on the volume of the gas.

8. The process of claim 1, wherein the molecular oxygen or the molecular oxygen-containing gas is fed into the reaction system at a rate of about 0.75 to about 1.3 N m³ per kg of the p-dialkylbenzene as a molecular oxygen.

9. The process of claim 1, wherein the molecular oxygen-containing gas is air and the air is fed at a rate of 3.8 to 6.0 N m³ per kg of the p-dialkylbenzene.

10. The process of claim 1, wherein the oxidation catalyst includes bromine and at least one heavy metal selected from the group consisting of cobalt, manganese, copper, nickel, chromium, iron, zinc, cadmium, cerium and lead.

11. The process of claim 1, wherein the amount of the oxidation catalyst is such that the amount of the heavy metal is about 0.01 to about 3.0% by weight, calculated as the metal, based on the weight of the lower aliphatic carboxylic acid solvent.

12. The process of claim 10, wherein the amount of bromine in the oxidation catalyst, as atomic bromine, is about 1 to about 8 times the weight of the catalytic heavy metal.

13. The process of claim 10, wherein the oxidation catalyst contains cobalt in an amount of about 0.01 to about 0.5% by weight, calculated as the metal, based on the weight of the lower aliphatic carboxylic acid solvent, manganese in an amount of about 1 to about 500%, calculated as the metal, based on the weight of the cobalt and bromine in an amount of about 1 to about 8 times, as atomic bromine, the weight of the total weight of the cobalt and the manganese.

14. The process of claim 1, wherein the lower aliphatic carboxylic acid contains 1 to 8 carbon atoms.

15. The process of claim 14, wherein the lower aliphatic carboxylic acid is acetic acid.

16. The process of claim 1, wherein the lower aliphatic carboxylic acid is present in an amount of more than about 2 times the weight of the p-dialkylbenzene and/or the weight of the oxidized intermediate thereof, calculated as weight of p-dialkylbenzene.

17. The process of claim 1, wherein the lower aliphatic carboxylic acid is present in an amount of 3 to 6 times the weight of the p-dialkylbenzene and/or the weight of the oxidized intermediate thereof, calculated as weight of p-dialkylbenzene.

18. The process of claim 1, wherein the reaction pressure is a pressure sufficient to maintain the reaction components in the liquid phase.

19. The process of claim 1, wherein the phenol is a monohydric phenol.

20. The process of claim 1, wherein the phenol is a monohydric phenol having at least one phenolic hydroxyl group, which phenol may be unsubstituted or substituted with one or more alkyl groups having 1 to 3 carbon atoms.

21. The process of claim 1, wherein the phenol is selected from the group consisting of phenol, cresol, dimethylphenol, n-propylphenol and a mixture thereof.

22. The process of claim 1, wherein the phenol is selected from the group consisting of hydroquinone, resorcinol, catechol, pyrogallol, methylhydroquinone, ethylhydroquinone, isopropylhydroquinone, n-propylhydroquinone and a mixture thereof.

23. The process of claim 1, wherein the phenol is a polyhydric phenol.

* * * * *